United States Patent [19]

Mauvernay et al.

[11] 4,035,498

[45] July 12, 1977

[54] PHARMACEUTICALLY ACTIVE COMPOUNDS AND THE PREPARATION THEREOF

[75] Inventors: Roland Yves Mauvernay, Riom; Norbert Busch, Loubeyrat; Jacques Moleyre, Mozac; Jacques Simond, Chamalieres; André Monteil, Gerzat, all of France

[73] Assignee: Centre Europeen de Recherches Mauvernay, Riom, France

[21] Appl. No.: 617,576

[22] Filed: Sept. 29, 1975

[30] Foreign Application Priority Data

Sept. 30, 1974 France .............................. 74.32806

[51] Int. Cl.$^2$ ............. C07D 405/06; C07D 295/08; A61K 31/495
[52] U.S. Cl. ........................ 424/250; 260/268 BC
[58] Field of Search ............. 260/268 BC; 424/250

[56] References Cited

U.S. PATENT DOCUMENTS 3,753,985  8/1973  Gavin et al. ................ 260/247.7 G Primary Examiner—Donald G. Daus
Assistant Examiner—Jose Tovar

[57] ABSTRACT

Compounds of the formula:

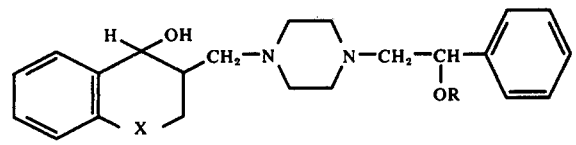

wherein R is a lower alkyl group, X is oxygen or the group —$(CH_2)_n$— where $n$ is 0 or 1, having bronchospasmolytic activity, are described.

7 Claims, No Drawings

PHARMACEUTICALLY ACTIVE COMPOUNDS AND THE PREPARATION THEREOF

This invention relates to new aminoalcohols, the preparation thereof, and pharmaceutical compositions containing them.

It has now been found, in accordance with the present invention that certain aminoalcohols, as defined below, have bronchospasmolytic activity.

According to the invention, therefore, there are provided as new compounds aminoalcohols of the general formula:

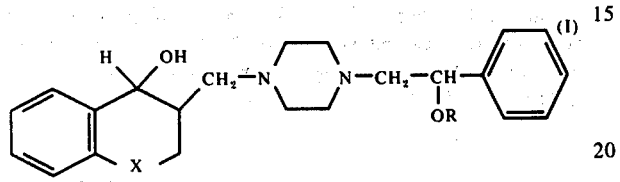

in which
R represents a lower alkyl group and
X represents an oxygen atom or a group $-(CH_2)_n-$, in which $n$ is 0 or 1.

In French BSM No. 7304 M we have already described, as compounds having bronchospasmlytic activity, compounds of the general formula:

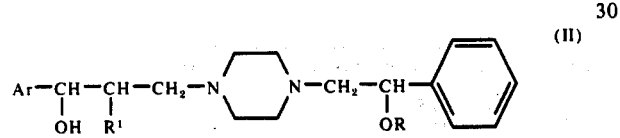

in which
Ar represents an aromatic residue and
$R^1$ and $R^2$ each represent an alkyl radical.

The compounds in accordance with the present invention have a structure which approaches that of the compounds of Formula II but which is fundamentally distinguished therefrom by the fact that the secondary alcohol function is attached to a cyclic structure and not to a linear chain.

This structural modification was only made possible by the development of a synthetic route different from that used for the preparation of the compounds of Formula II. Accordingly, another object of the invention resides in the particular process used to obtain the compounds of Formula I. This process is carried out in three successive stages as follows.

In the first stage a benzocyclanone, dimethylamine and paraformaldehyde are subjected to Mannich condensation in accordance with the following reaction scheme:

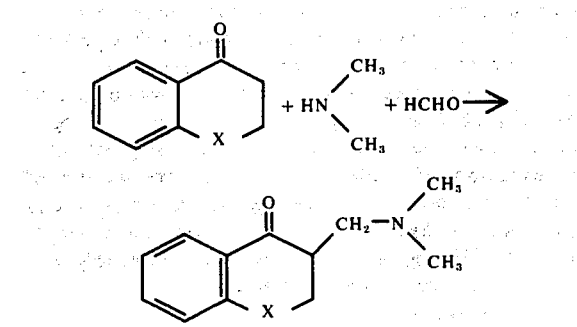

In the second stage, the product obtained in the first stage is subjected to transamination in the presence of an N-(-2-phenyl-2-alkoxy)-ethyl piperazine in an aromatic solvent such as benzene, according to the reaction scheme:-

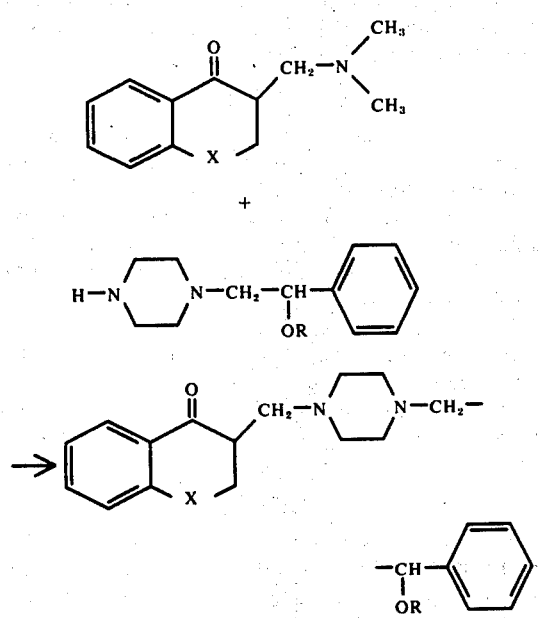

The substituted piperazine used in the second stage is advantageously prepared as described in French Pat. No. 5,390 M.

In the third stage, the aminoketone obtained in the second stage is reduced to the corresponding aminoalcohol by the action of lithium aluminium hydride in the presence of anhydrous ether, according to the reaction scheme:

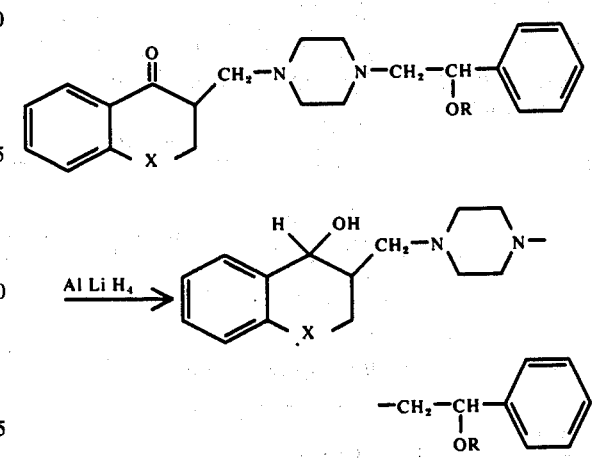

For a better understanding of the process of the invention there is now given a detailed description of the synthesis of 2-[4-(2-methoxy-2-phenyl)ethyl piperazinyl] methyl tetralol.

1st Stage

A mixture of 43.8 g (0.3 mole) of tetralone, 28.2 g (0.35 mole) of dimethylamine hydrochloride and 10.5 g (0.35 mole) of trioxymethylene in 100 ml of absolute ethanol to which has been added a drop concentrated hydrochloric acid, is refluxed for 1 hour.

After refluxing for 1 hour, 5 g of trioxymethylene are added to the reaction mixture and the whole mixture then refluxed for a further six hours. The reaction mixture is then concentrated to one-third of its volume and the precipitate obtained washed with warm acetone, dried and then used as such in the following stage. The product is obtained in yield of 28 g corresponding to 64% of the theoretical yield.

2nd Stage

A mixture of 28 g (0.116 mole) of the compound obtained in the first stage and 13.2 g (0.06 mole) of 2-(methoxy-2-phenyl)-ethyl piperazine in 30 ml of benzene is refluxed for about 20 hours. The dimethylamine hydrochloride precipitate is filtered off and washed with benzene. The resulting benzene solutions are then concentrated.

The crystalline base obtained is then recrystallised from isopropanol (melting point = 110° C). Treatment with alcohol saturated with hydrochloric acid leads, after elaboration, to 23 g (86% theoretical) of 2-[4-(2-methoxy-2-phenyl)ethyl piperazinyl] methyl tetralone dihydrochloride.

3rd Stage 8.4 G (0.2 mole) of lithium aluminium hydride is suspended in 200 ml of anhydrous ether and there is thereto, in small amounts, 23 g (0.05 mole) of the dihydrochloride obtained in the second stage. The mixture is then refluxed for 20 hours. The excess hydride is destroyed by the addition of ethyl acetate followed by water saturated with ammonium chloride. After extraction there is obtained 18.4 g of the title compound in the form of the crude base (quantitative yield). The dihydrochloride is formed by the action of ethanol saturated with hydrogen chloride and is recrystallised from isopropanol to give a compound having a melting point of 242° C and a hydrogen chloride content of 15.98% (theoretical content 16.10%).

Table 1 below gives the characteristics of a number of compounds in accordance with the invention obtained by the same procedure using appropriate starting materials.

The animals were removed from the enclosure when they fell into asphyxic syncope and the period of exposure was noted. This value was taken as a control value since, 24 hours later, the same animals were treated, by the oral route, with the compound under test. 45 minutes after treatment they were again subjected the aerosol. The animals which resisted ten minutes longer then previously were considered to be protected by the treatment.

The product under test was administered to lots of animals. The first dose used was 50 mg/kg P.O. If the product proved to be active, the dosages were reduced in order to ascertain the $ED_{50}$ by the linearisation method.

The results obtained are shown in Table II where there is also given the acute toxicity in mice by the oral route evaluated according to the method of Behrens and Karber (Arch. Exp. Path Pharm. 177, 379, 1935).

| Compound No. | Bronchospasmolytic Activity | | $ED_{50}$ (mg/kg P.O.) | Acute toxicity mg/kg P.O. |
|---|---|---|---|---|
| | 50 mg/kg P.O. | | | |
| | Activity | N | | |
| 1 | 70 | 10 | | ≠ 400 |
| 2 | 100* | 10 | 4.9]4.3/7.1[ | ≠ 400 |
| 3 | 100* | 5 | 1.6]0.9/2.9[ | ≠ 300 |
| 4 | 100* | 5 | 9.3]6.8/12.8[ | ≠ 300 |
| Dextromethorphan | 0** | 10 | | |
| Diphenhydramine | 93 | 15 | 4.5]3.4/5.9[ | |
| | 10 mg/kg | | | |

$ED_{50}$:Effective dose 50 calculated by the linearisation method
] [:5% confidence limits for $ED_{50}$
*:Dose used: 25 mg/kg P.O.
**:Dose used: 100 mg/kg P.O.

These results show that the compounds studied have good bronchospasmolytic activity.

Complementary tests, in particular the Domenjoz test (Arch. Exp. Pathol. v. Pharmacol. 215,19, 1952), have also shown an antitussive activity, in particular for compound No. 2 in the case of which a coughing reduction of 83% was noted at a dosage of 20 mg/kg by the intraduodenal route.

TABLE 1

| Compound No. | X | R | Salt | M.p. | M.W. | | C% | H% | N% |
|---|---|---|---|---|---|---|---|---|---|
| 1 | —O— | —CH₃ | 2 HCl | 303° C | 455.44 | Calculated | 60.65 | 5.57 | 4.56 |
| | | | | | | Found | 61.2 | 5.32 | 4.54 |
| 2 | —CH₂— | —C₂H₅ | 2 HCl | 220° C | 465.5 | Calculated | 64.23 | 7.76 | 5.50 |
| | | | | | | Found | 62.80 | 7.84 | 5.90 |
| 3 | —CH₂— | —CH₃ | 2 HCl | 242° C | 453.47 | Calculated | 63.57 | 7.55 | 6.18 |
| | | | | | | Found | 62.92 | 7.42 | 6.24 |
| 4 | — | —CH₃ | 2 HCl | 210° C | 438.43 | Calculated | 63.01 | 7.13 | 6.39 |
| | | | | | | Found | 62.57 | 7.40 | 6.27 |

NOTE:

For Compound No. 4, the group X is a group —(CH₂.)₀— that is a simple carbon bond so that the ring containing it is a ring containing five carbon atoms.

The bronchospasmolytic properties of the compounds of the investigated by the following pharmacological tests:

1. Histaminic bronchospasm in the Guinea Pig

The histamine aerosol technique was employed.

The guinea pigs, of either sex and weighing from 250 to 400 g, were placed in an enclosure in which circulated a 0.3% aerosol of histamine in a 20% mixture of distilled water and glycerine.

The invention also provides, accordingly, a pharmaceutical composition comprising a compound in accordance with the invention in association with a pharmaceutical carrier or diluent. These compositions may be used in the treatment of bronchopulmonary conditions, generally at daily dosages of from 10 to 500 mg of active compound. The pharmaceutical compositions of the invention will preferably be in the form of compositions for oral administration, e.g. tablets, dragees, capsules and the like which may contain, for example, from 5 to 250 mg of active compound, preferably from 10 to 100 mg of active compound.

What we claim is:

1. A compound selected from the group consisting of those of the formula:

(I) 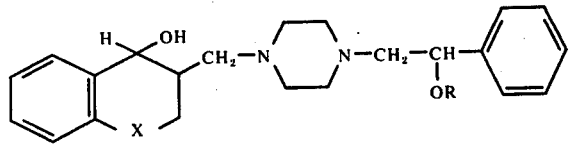

and pharmaceutically acceptable acid addition salts thereof, in which R represents a methyl or ethyl group and X represents an oxygen atom or a group —(CH$_2$)$_n$— in which $n$ is 0 or 1.

2. 3[4-(2-Methoxy-2-phenyl)-ethyl piperazinyl] methyl-4-hydroxy -chromane.

3. 2-[4-(2-Ethoxy 2-phenyl)-ethyl-piperazinyl] -methyl-tetralol.

4. 2-[4-(2-Methoxy 2-phenyl)ethyl piperazinyl] -methyl tetralol.

5. 1-Hydroxy-2-[4-(2-methoxy 2-phenyl)ethyl- piperazinyl] methyl indane.

6. A pharmaceutical composition consisting essentially of a compound as claimed in claim 1 in association with a pharmaceutical carrier or diluent.

7. The application of a compound as claimed in claim 1 in the treatment of bronchopulmonary conditions in the form of orally administrable compositions at daily dosages of from 10 to 500 mg.